United States Patent [19]

Payne et al.

[11] Patent Number: 5,407,825
[45] Date of Patent: Apr. 18, 1995

[54] BACILLUS THURINGIENSIS ISOLATES ACTIVE AGAINST LEPIDOPTERAN PESTS, AND GENES ENCODING NOVEL LEPIDOPTERAN-ACTIVE TOXINS

[75] Inventors: Jewel Payne, San Diego; August J. Sick, Oceanside, both of Calif.

[73] Assignee: Mycogen Corp., San Diego, Calif.

[21] Appl. No.: 40,751

[22] Filed: Mar. 29, 1993

Related U.S. Application Data

[60] Division of Ser. No. 904,243, Jun. 25, 1992, Pat. No. 5,206,166, which is a division of Ser. No. 451,389, Dec. 14, 1989, Pat. No. 5,164,180, which is a continuation-in-part of Ser. No. 353,860, May 18, 1989, abandoned.

[51] Int. Cl.$^6$ .................. A01N 63/00; C12N 1/21; C12N 1/20; C07K 13/00
[52] U.S. Cl. .................. 435/252.34; 424/93.2; 424/93.21; 424/93.461; 435/252.3; 435/252.31; 435/252.33; 435/252.35; 435/252.5; 530/350; 530/825

[58] Field of Search ................ 424/93 L, 93 A, 93 B, 424/93.2, 93.21, 93.461; 435/69.1, 71.2, 172.3, 252.3, 252.31, 252.33, 2582.34, 252.35, 252.5; 530/350, 825

[56] References Cited

U.S. PATENT DOCUMENTS 4,695,455  9/1987  Barns et al. ................ 435/69.1

*Primary Examiner*—Richard A. Schwartz
*Assistant Examiner*—Nancy T. Vogel
*Attorney, Agent, or Firm*—Saliwanchik & Saliwanchik

[57] ABSTRACT

Novel *Bacillus thuringiensis* genes encoding toxins which are active against lepidopteran insects have been cloned from novel lepidopteran-active *B. thuringiensis* microbes. The DNA encoding the *B. thuringiensis* toxins can be used to transform various prokaryotic and eukaryotic microbes to express the *B. thuringiensis* toxins. These recombinant microbes can be used to control lepidopteran insects in various environments.

13 Claims, 1 Drawing Sheet

Figure 1

A. *Bacillus thuringiensis* HD-1
B. *Bacillus thuringiensis* PS81RR1
C. *Bacillus thuringiensis* PS81A2
D. *Bacillus thuringiensis* HD-1

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1179 amino acids
( B ) TYPE: amino acid
( C ) STRANDEDNESS: single
( D ) TOPOLOGY: linear (ii) MOLECULE TYPE: protein (iii) HYPOTHETICAL: YES (iv) ANTI-SENSE: NO (vi) ORIGINAL SOURCE:
    (A) ORGANISM: BACILLUS THURINGIENSIS
    (B) STRAIN: AIZAWAI
    (C) INDIVIDUAL ISOLATE: PS81I (vii) IMMEDIATE SOURCE:
    (A) LIBRARY: LAMBDAGEM (TM) - 11 LIBRARY OF AUGUST SICK
    (B) CLONE: 81RR1

(xi) SEQUENCE DESCRIPTION: SEQ ID NO:1:

```
Met Glu Ile Met Asn Asn Gln Asn Gln Cys Val Pro Tyr Asn Cys Leu
 1               5                  10                  15

Asn Asp Pro Thr Ile Glu Ile Leu Glu Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Ile Asp Leu Ile
    50                  55                  60

Trp Gly Phe Val Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ala Phe Arg Glu Trp Glu Ala Asp Pro Thr Asn Pro Ala Leu Thr Glu
    115                 120                 125

Glu Met Arg Ile Gln Phe Asn Asp Met Asn Ser Ala Leu Thr Thr Ala
130                 135                 140

Ile Pro Leu Phe Thr Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Val Ala Thr Ile Asn Ser Arg
            180                 185                 190

Tyr Asn Asp Leu Thr Arg Leu Ile Gly Thr Tyr Thr Asp Tyr Ala Val
        195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Leu Leu Asn Ser Ile Thr
290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ala Gly Pro Glu Phe Thr Phe Pro
            325                 330                 335

Arg Tyr Gly Thr Met Gly Asn Ala Ala Pro Pro Val Leu Ile Ser Thr
        340                 345                 350
```

-continued

```
Thr Gly Leu Gly Ile Phe Arg Thr Leu Ser Ser Pro Leu Tyr Arg Arg
        355             360             365
Ile Ile Leu Gly Ser Gly Pro Asn Asn Gln Asn Leu Phe Val Leu Asp
370             375             380
Gly Thr Glu Phe Ser Phe Ala Ser Leu Thr Ala Asp Leu Pro Ser Thr
385             390             395             400
Ile Tyr Arg Gln Arg Gly Thr Val Asp Ser Leu Asp Val Ile Pro Pro
            405             410             415
Gln Asp Asn Ser Val Pro Ala Arg Ala Gly Phe Ser His Arg Leu Ser
            420             425             430
His Val Thr Met Leu Ser Gln Ala Ala Gly Ala Val Tyr Thr Leu Arg
            435             440             445
Ala Pro Thr Phe Ser Trp Arg His Arg Ser Ala Glu Phe Ser Asn Leu
450             455             460
Ile Pro Ser Ser Gln Ile Thr Gln Ile Pro Leu Thr Lys Ser Ile Asn
465             470             475             480
Leu Gly Ser Gly Thr Ser Val Val Lys Gly Pro Gly Phe Thr Gly Gly
            485             490             495
Asp Ile Leu Arg Ile Thr Ser Pro Gly Gln Ile Ser Thr Leu Arg Val
            500             505             510
Thr Ile Thr Ala Pro Leu Ser Gln Arg Tyr Arg Val Arg Ile Arg Tyr
        515             520             525
Ala Ser Thr Thr Asn Leu Gln Phe His Thr Ser Ile Asp Gly Arg Pro
    530             535             540
Ile Asn Gln Gly Asn Phe Ser Ala Thr Met Ser Ser Gly Gly Asn Leu
545             550             555             560
Gln Ser Gly Ser Phe Arg Thr Ala Gly Phe Thr Thr Pro Phe Asn Phe
            565             570             575
Ser Asn Gly Ser Ser Ile Phe Thr Leu Ser Ala His Val Phe Asn Ser
        580             585             590
Gly Asn Glu Val Tyr Ile Glu Arg Ile Glu Phe Val Pro Ala Glu Val
        595             600             605
Thr Phe Glu Ala Glu Tyr Asp Leu Glu Arg Ala Gln Glu Ala Val Asn
610             615             620
Ala Leu Phe Thr Ser Ser Asn Gln Leu Gly Leu Lys Thr Asn Val Thr
625             630             635             640
Asp Tyr His Ile Asp Gln Val Ser Asn Leu Val Glu Cys Leu Ser Gly
            645             650             655
Glu Phe Cys Leu Asp Glu Lys Arg Glu Leu Ser Glu Lys Val Lys His
            660             665             670
Ala Asn Arg Leu Ser Asp Glu Arg Asn Leu Leu Gln Asp Pro Asn Phe
        675             680             685
Arg Gly Ile Asn Arg Gln Pro Asp Arg Gly Trp Arg Gly Ser Thr Asp
    690             695             700
Ile Thr Ile Gln Gly Gly Asp Asp Val Phe Lys Glu Asn Tyr Val Thr
705             710             715             720
Leu Pro Gly Thr Phe Asn Glu Cys Tyr Pro Thr Tyr Leu Tyr Gln Lys
            725             730             735
Ile Asp Glu Ser Lys Leu Lys Ala Tyr Thr Arg Tyr Gln Leu Arg Gly
            740             745             750
Tyr Ile Glu Asp Ser Gln His Leu Glu Ile Tyr Leu Ile Arg Tyr Asn
        755             760             765
Thr Lys His Glu Thr Val Asn Val Pro Gly Thr Gly Ser Leu Trp Pro
770             775             780
```

| | | | | | | | | | | | | | | |
|---|---|---|---|---|---|---|---|---|---|---|---|---|---|---|
|Leu|Ser|Val|Glu|Asn|Pro|Ile|Gly|Lys|Cys|Gly|Glu|Pro|Asn|Arg|Cys|
|785| | | | |790| | | |795| | | | |800|
|Ala|Pro|Gln|Leu|Glu|Trp|Asn|Pro|Asp|Leu|Asp|Cys|Ser|Cys|Arg|Asp|
| | | | |805| | | |810| | | | |815| |
|Gly|Glu|Lys|Cys|Ala|His|His|Ser|His|His|Phe|Ser|Leu|Asp|Ile|Asp|
| | | |820| | | |825| | | | |830| | |
|Ile|Gly|Cys|Thr|Asp|Leu|Asn|Glu|Asn|Leu|Gly|Val|Trp|Val|Ile|Phe|
| | |835| | | | |840| | | | |845| | |
|Lys|Ile|Lys|Met|Gln|Asp|Gly|His|Ala|Arg|Leu|Gly|Asn|Leu|Glu|Phe|
| |850| | | | |855| | | | |860| | | |
|Leu|Glu|Glu|Lys|Pro|Leu|Val|Gly|Glu|Ser|Leu|Ala|Arg|Val|Lys|Arg|
|865| | | | |870| | | |875| | | | |880| |
|Ala|Glu|Lys|Lys|Trp|Arg|Asp|Lys|Arg|Glu|Lys|Leu|Gln|Val|Glu|Thr|
| | | | |885| | | |890| | | | |895| | |
|Asn|Ile|Val|Tyr|Lys|Glu|Ala|Lys|Glu|Ser|Val|Asp|Ala|Leu|Phe|Val|
| | |900| | | | |905| | | | |910| | |
|Asn|Ser|Gln|Tyr|Asp|Arg|Leu|Gln|Ala|Asp|Thr|Asp|Ile|Ala|Met|Ile|
| | |915| | | | |920| | | | |925| | |
|His|Ala|Ala|Asp|Lys|Arg|Val|His|Arg|Ile|Arg|Glu|Ala|Tyr|Leu|Pro|
| |930| | | | |935| | | | |940| | | |
|Glu|Leu|Ser|Val|Ile|Pro|Gly|Val|Asn|Ala|Gly|Ile|Phe|Glu|Glu|Leu|
|945| | | | |950| | | |955| | | | |960| |
|Glu|Gly|Arg|Ile|Phe|Thr|Ala|Tyr|Ser|Leu|Tyr|Asp|Ala|Arg|Asn|Val|
| | | |965| | | | |970| | | | |975| | |
|Ile|Lys|Asn|Gly|Asp|Phe|Asn|Asn|Gly|Leu|Ser|Cys|Trp|Asn|Val|Lys|
| | | |980| | | | |985| | | | |990| | |
|Gly|His|Val|Asp|Val|Glu|Glu|Gln|Asn|Asn|His|Arg|Ser|Val|Leu|Val|
| | |995| | | | |1000| | | | |1005| | |
|Val|Pro|Glu|Trp|Glu|Ala|Glu|Val|Ser|Gln|Glu|Val|Arg|Val|Cys|Pro.|
| |1010| | | | |1015| | | | |1020| | | |
|Gly|Arg|Gly|Tyr|Ile|Leu|Arg|Val|Thr|Ala|Tyr|Lys|Glu|Gly|Tyr|Gly|
|1025| | | | |1030| | | |1035| | | | |1040| |
|Glu|Gly|Cys|Val|Thr|Ile|His|Glu|Ile|Glu|Asp|Asn|Thr|Asp|Glu|Leu|
| | | |1045| | | | |1050| | | | |1055| | |
|Lys|Phe|Ser|Asn|Cys|Val|Glu|Glu|Glu|Val|Tyr|Pro|Asn|Asn|Thr|Val|
| | | |1060| | | | |1065| | | | |1070| | |
|Thr|Cys|Asn|Asp|Tyr|Thr|Ala|Asn|Gln|Glu|Glu|Tyr|Gly|Gly|Ala|Tyr|
| | | |1075| | | | |1080| | | | |1085| | |
|Thr|Ser|Arg|Asn|Arg|Gly|Tyr|Gly|Glu|Ser|Tyr|Glu|Ser|Asn|Ser|Ser|
| | | |1090| | | | |1095| | | | |1100| | |
|Ile|Pro|Ala|Glu|Tyr|Ala|Pro|Val|Tyr|Glu|Glu|Ala|Tyr|Ile|Asp|Gly|
|1105| | | | |1110| | | | |1115| | | | |1120|
|Arg|Lys|Glu|Asn|Pro|Cys|Glu|Ser|Asn|Arg|Gly|Tyr|Gly|Asp|Tyr|Thr|
| | | | |1125| | | |1130| | | | |1135| | |
|Pro|Leu|Pro|Ala|Gly|Tyr|Val|Thr|Lys|Glu|Leu|Glu|Tyr|Phe|Pro|Glu|
| | | |1140| | | | |1145| | | | |1150| | |
|Thr|Asp|Lys|Val|Trp|Ile|Glu|Ile|Gly|Glu|Thr|Glu|Gly|Thr|Phe|Ile|
| | |1155| | | | |1160| | | | |1165| | | |
|Val|Asp|Ser|Val|Glu|Leu|Leu|Leu|Met|Glu|Glu| | | | | |
| | |1170| | | | |1175| | | | | | | | |

( 2 ) INFORMATION FOR SEQ ID NO:2:

( i ) SEQUENCE CHARACTERISTICS:
        ( A ) LENGTH: 3537 base pairs
        ( B ) TYPE: nucleic acid
        ( C ) STRANDEDNESS: double ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Bacillus thuringiensis
            ( B ) STRAIN: aizawai
            ( C ) INDIVIDUAL ISOLATE: PS81I ( v i i ) IMMEDIATE SOURCE:
( A ) LIBRARY: LAMBDAGEM - 11 (tm) LIBRARY OF AUGUST SICK
( B ) CLONE: 81RR1

( x i ) SEQUENCE DESCRIPTION: SEQ ID NO:2:

```
ATGGAGATAA TGAATAATCA GAATCAATGC GTTCCTTATA ACTGTTTGAA TGATCCGACA 60
ATTGAAATAT TAGAAGGAGA AAGAATAGAA ACTGGTTACA CCCCAATAGA TATTTCCTTG 120
TCGCTAACGC AATTTCTGTT GAGTGAATTT GTCCCAGGTG CTGGGTTTGT ATTAGGTTTA 180
ATTGATTTAA TATGGGGGTT TGTGGGTCCC TCTCAATGGG ATGCATTTCT TGTGCAAATT 240
GAACAGTTAA TTAACCAAAG AATAGAGGAA TTCGCTAGGA ACCAAGCAAT TTCTAGATTA 300
GAAGGGCTAA GCAACCTTTA TCAAATTTAC GCAGAAGCTT TTAGAGAGTG GGAAGCAGAT 360
CCTACTAATC CAGCATTAAC AGAAGAGATG CGTATTCAGT TCAATGACAT GAACAGTGCT 420
CTTACAACCG CTATTCCTCT TTTTACAGTT CAAAATTATC AAGTACCTCT TCTATCAGTA 480
TATGTTCAAG CTGCAAATTT ACATTTATCG GTTTTGAGAG ATGTTTCAGT GTTTGGACAA 540
CGTTGGGGAT TTGATGTAGC AACAATCAAT AGTCGTTATA ATGATTTAAC TAGGCTTATT 600
GGCACCTATA CAGATTATGC TGTACGCTGG TATAATACGG GATTAGAACG TGTATGGGGA 660
CCGGATTCTA GAGATTGGGT AAGGTATAAT CAATTTAGAA GAGAGCTAAC ACTAACTGTA 720
TTAGATATCG TTTCTCTGTT CCCGAACTAT GATAGTAGAA CGTATCCAAT TCGAACAGTT 780
TCCCAATTAA CTAGAGAAAT TTATACAAAC CCAGTATTAG AAAATTTTGA TGGTAGTTTT 840
CGTGGAATGG CTCAGAGAAT AGAACAGAAT ATTAGGCAAC CACATCTTAT GGATCTCCTT 900
AATAGTATAA CCATTTATAC TGATGTGCAT AGAGGCTTTA ATTATTGGTC AGGACATCAA 960
ATAACAGCTT CTCCTGTCGG TTTTGCGGGG CCAGAATTTA CTTTTCCTAG ATATGGAACC 1020
ATGGGAAATG CTGCTCCACC CGTACTGATC TCAACTACTG GTTTGGGGAT TTTTAGAACA 1080
TTATCTTCAC CTCTTTACAG AAGAATTATA CTTGGTTCAG GCCCAAATAA TCAGAACCTG 1140
TTTGTCCTTG ATGGAACGGA ATTTTCTTTT GCCTCCCTAA CAGCCGATTT ACCTTCTACT 1200
ATATACAGAC AAAGGGGAAC GGTCGATTCA CTAGATGTAA TACCGCCACA GGATAATAGT 1260
GTGCCAGCAC GTGCGGGATT TAGTCATCGA TTAAGTCATG TTACAATGCT GAGCCAAGCA 1320
GCTGGAGCAG TTTACACCTT GAGAGCTCCA ACGTTTTCTT GGCGACATCG TAGTGCTGAA 1380
TTCTCTAACC TAATTCCTTC ATCACAAATC ACACAGATAC CTTTAACAAA GTCTATTAAT 1440
CTTGGCTCTG GGACCTCTGT TGTTAAAGGA CCAGGATTTA CAGGAGGAGA TATTCTTCGA 1500
ATAACTTCAC CTGGCCAGAT TTCAACCTTA AGAGTGACTA TTACGGCACC ATTATCACAA 1560
AGATATCGCG TAAGAATTCG CTACGCTTCT ACTACAAATT TACAATTCCA TACATCAATT 1620
GACGGAAGAC CTATTAATCA GGGGAATTTT TCAGCAACTA TGAGTAGTGG GGGTAATTTA 1680
CAGTCCGGAA GCTTTAGGAC TGCAGGTTTT ACTACTCCGT TTAACTTTTC AAATGGATCA 1740
AGTATATTTA CGTTAAGTGC TCATGTCTTC AATTCAGGCA ATGAAGTTTA TATAGAGCGA 1800
ATTGAATTTG TTCCGGCAGA AGTAACATTT GAGGCGGAAT ATGATTTAGA AAGAGCGCAA 1860
GAGGCGGTGA ATGCTCTGTT TACTTCTTCC AATCAACTAG GATTAAAAAC AAATGTGACG 1920
```

```
GACTATCATA TTGATCAAGT GTCCAATCTA GTCGAATGTT TATCCGGTGA ATTCTGTCTG   1980
GATGAAAAGA GAGAATTGTC CGAGAAAGTC AAACATGCGA ACCGACTCAG TGATGAGCGG   2040
AATTTACTTC AAGACCCAAA CTTCAGAGGC ATCAATAGAC AACCAGACCG TGGCTGGAGA   2100
GGCAGTACGG ATATTACCAT CCAAGGAGGA GATGACGTAT TCAAAGAGAA TTACGTCACA   2160
CTACCGGGTA CCTTTAATGA GTGTTATCCT ACGTATCTGT ATCAAAAAT  AGATGAGTCG   2220
AAATTAAAAG CCTATACCCG TTACCAATTA AGAGGGTACA TCGAGGATAG TCAACACTTA   2280
GAAATCTATT TAATTCGCTA CAATACAAAA CACGAAACAG TAAATGTGCC AGGTACGGGT   2340
TCCTTATGGC CGCTTTCAGT CGAAAATCCA ATTGGAAAGT GCGGAGAACC AAATCGATGC   2400
GCACCACAAC TTGAATGGAA TCCTGATCTA GATTGTTCCT GCAGAGACGG GAAAAATGT   2460
GCACATCACT CCCATCATTT CTCCTTGGAC ATTGATATTG GATGTACAGA TTTAATGAG   2520
AACTTAGGTG TATGGGTGAT ATTCAAAATT AAGATGCAAG ATGGTCACGC AAGACTAGGT   2580
AATCTAGAGT TTCTCGAAGA GAAACCATTA GTAGGCGAAT CGTTAGCACG CGTGAAGAGA   2640
GCGGAGAAGA AGTGGAGAGA CAAACGAGAG AAATTGCAAG TGGAAACAAA TATCGTTTAT   2700
AAAGAGGCAA AGAATCTGT  AGATGCTTTA TTTGTGAACT CTCAATATGA TAGATTACAA   2760
GCGGATACCG ACATCGCGAT GATTCATGCG GCAGATAAAC GCGTTCATCG AATTCGAGAA   2820
GCATATCTTC CAGAGTTATC TGTAATTCCG GGTGTCAATG CGGGCATTTT TGAAGAATTA   2880
GAGGGACGTA TTTTCACAGC CTACTCTTTA TATGATGCGA GAAATGTCAT TAAAAATGGC   2940
GATTTCAATA ATGGCTTATC ATGCTGGAAC GTGAAGGGC  ATGTAGATGT AGAAGAACAA   3000
AACAACCACC GTTCGGTTCT TGTTGTCCCG GAATGGGAAG CAGAGGTGTC ACAAGAGGTT   3060
CGTGTCTGTC CAGGTCGTGG CTATATCCTA CGTGTTACAG CGTACAAAGA GGGATATGGA   3120
GAAGGTTGCG TAACGATTCA TGAGATCGAA GACAATACAG ACGAACTGAA ATTCAGCAAC   3180
TGTGTAGAAG AGGAAGTATA TCCAAACAAC ACGGTAACGT GTAATGATTA TACTGCAAAT   3240
CAAGAAGAAT ACGGGGGTGC GTACACTTCT CGTAATCGTG GATATGGTGA ATCTTATGAA   3300
AGTAATTCTT CCATACCAGC TGAGTATGCG CCAGTTTATG AGGAAGCATA TAGAGATGGA   3360
AGAAAAGAGA ATCCTTGTGA ATCTAACAGA GGATATGGGG ATTACACGCC ACTACCAGCT   3420
GGTTATGTGA CAAAAGAATT AGAGTACTTC CCAGAAACCG ATAAGGTATG GATTGAGATC   3480
GGGGAAACGG AAGGAACATT CATCGTGGAT AGCGTGGAAT TACTCCTTAT GGAGGAA     3537
```

( 2 ) INFORMATION FOR SEQ ID NO:3:

( i ) SEQUENCE CHARACTERISTICS:
        ( A ) LENGTH: 1174 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Bacillus thuringiensis
        ( B ) STRAIN: aizawai
        ( C ) INDIVIDUAL ISOLATE: PS81A2

( v i i ) IMMEDIATE SOURCE:
        ( A ) LIBRARY: Lambdagem - 11 (tm) Library of August Sick
        ( B ) CLONE: 81A2

( x i ) SEQUENCE DESCRIPTION: SEQ ID NO:3:

Met Glu Asn Asn Ile Glu Asn Gln Cys Ile Pro Tyr Asn Cys Leu Asn

-continued

| 1 | | | | 5 | | | | | 10 | | | | | 15 | |
|---|---|---|---|---|---|---|---|---|---|---|---|---|---|---|---|
| Asn | Pro | Glu | Val | Glu | Ile | Leu | Gly | Ile | Glu | Arg | Ser | Asn | Ser | Asn | Val |
| | | | 20 | | | | | 25 | | | | 30 | | | |
| Ala | Ala | Glu | Ile | Gly | Leu | Gly | Leu | Ser | Arg | Leu | Leu | Val | Ser | Arg | Ile |
| | | | 35 | | | | 40 | | | | | 45 | | | |
| Pro | Leu | Gly | Asp | Phe | Ile | Leu | Gly | Leu | Phe | Asp | Val | Ile | Trp | Gly | Ala |
| | | | 50 | | | | 55 | | | | | 60 | | | |
| Ile | Gly | Pro | Ser | Gln | Trp | Asp | Ile | Phe | Leu | Glu | Gln | Ile | Glu | Leu | Leu |
| 65 | | | | | 70 | | | | | 75 | | | | | 80 |
| Ile | Gly | Gln | Arg | Ile | Glu | Glu | Phe | Ala | Arg | Asn | Gln | Ala | Ile | Ser | Arg |
| | | | | 85 | | | | | 90 | | | | | 95 | |
| Leu | Gln | Gly | Leu | Ser | Asn | Leu | Tyr | Arg | Ile | Tyr | Thr | Asn | Ala | Phe | Lys |
| | | | 100 | | | | | 105 | | | | | 110 | | |
| Asn | Trp | Glu | Val | Asp | Pro | Thr | Asn | Pro | Ala | Leu | Arg | Glu | Glu | Met | Arg |
| | | | 115 | | | | | 120 | | | | | 125 | | |
| Ile | Gln | Phe | Asn | Asp | Met | Asn | Ser | Ala | Leu | Thr | Thr | Ala | Ile | Pro | Leu |
| | | | 130 | | | | | 135 | | | | | 140 | | |
| Phe | Ser | Val | Gln | Gly | Tyr | Glu | Ile | Pro | Leu | Leu | Ser | Val | Tyr | Val | Gln |
| 145 | | | | | 150 | | | | | 155 | | | | | 160 |
| Ala | Ala | Asn | Leu | His | Leu | Ser | Val | Leu | Arg | Asp | Val | Ser | Val | Phe | Gly |
| | | | | 165 | | | | | 170 | | | | | 175 | |
| Gln | Arg | Trp | Gly | Phe | Asp | Val | Ala | Thr | Ile | Asn | Ser | Arg | Tyr | Asn | Asp |
| | | | 180 | | | | | 185 | | | | | 190 | | |
| Leu | Thr | Arg | Leu | Ile | Gly | Glu | Tyr | Thr | Asp | Tyr | Ala | Val | Arg | Trp | Tyr |
| | | 195 | | | | | 200 | | | | | 205 | | | |
| Asn | Thr | Gly | Leu | Asn | Arg | Leu | Pro | Arg | Asn | Glu | Gly | Val | Arg | Gly | Trp |
| | | 210 | | | | | 215 | | | | | 220 | | | |
| Ala | Arg | Phe | Asn | Arg | Phe | Arg | Arg | Glu | Leu | Thr | Ile | Ser | Val | Leu | Asp |
| 225 | | | | | 230 | | | | | 235 | | | | | 240 |
| Ile | Ile | Ser | Phe | Phe | Gln | Asn | Tyr | Asp | Ser | Arg | Leu | Tyr | Pro | Ile | Pro |
| | | | | 245 | | | | | 250 | | | | | 255 | |
| Thr | Ile | Tyr | Gln | Leu | Thr | Arg | Glu | Val | Tyr | Thr | Asp | Pro | Val | Ile | Asn |
| | | | 260 | | | | | 265 | | | | | 270 | | |
| Ile | Thr | Asp | Tyr | Arg | Val | Thr | Pro | Ser | Phe | Glu | Ser | Ile | Glu | Asn | Ser |
| | | 275 | | | | | 280 | | | | | 285 | | | |
| Ala | Ile | Arg | Ser | Pro | His | Leu | Met | Asp | Phe | Leu | Asn | Asn | Ile | Ile | Ile |
| | 290 | | | | | 295 | | | | | 300 | | | | |
| Asp | Thr | Asp | Leu | Ile | Arg | Gly | Val | His | Tyr | Trp | Ala | Gly | His | Arg | Val |
| 305 | | | | | 310 | | | | | 315 | | | | | 320 |
| Thr | Ser | His | Phe | Thr | Gly | Ser | Ser | Gln | Val | Ile | Ser | Ser | Pro | Gln | Tyr |
| | | | | 325 | | | | | 330 | | | | | 335 | |
| Gly | Ile | Thr | Ala | Asn | Ala | Glu | Pro | Ser | Arg | Thr | Ile | Ala | Pro | Ser | Thr |
| | | | 340 | | | | | 345 | | | | | 350 | | |
| Phe | Pro | Gly | Leu | Asn | Leu | Phe | Tyr | Arg | Thr | Leu | Ser | Asp | Pro | Phe | Phe |
| | | | 355 | | | | | 360 | | | | | 365 | | |
| Arg | Arg | Ser | Asp | Asn | Ile | Met | Pro | Thr | Leu | Gly | Ile | Asn | Val | Val | Gln |
| | | 370 | | | | | 375 | | | | | 380 | | | |
| Gly | Val | Gly | Phe | Ile | Gln | Pro | Asn | Asn | Gly | Glu | Val | Leu | Tyr | Arg | Arg |
| 385 | | | | | 390 | | | | | 395 | | | | | 400 |
| Arg | Gly | Thr | Val | Asp | Ser | Leu | Asp | Glu | Leu | Pro | Ile | Asp | Gly | Glu | Asn |
| | | | | 405 | | | | | 410 | | | | | 415 | |
| Ser | Leu | Val | Gly | Tyr | Ser | His | Arg | Leu | Ser | His | Val | Thr | Leu | Thr | Arg |
| | | | 420 | | | | | 425 | | | | | 430 | | |
| Ser | Leu | Tyr | Asn | Thr | Asn | Ile | Thr | Ser | Leu | Pro | Thr | Phe | Val | Trp | Thr |
| | | | 435 | | | | | 440 | | | | | 445 | | |

```
His His Ser Ala Thr Asp Arg Asn Ile Ile Tyr Pro Asp Val Ile Thr
    450                 455                 460
Gln Ile Pro Leu Val Lys Ser Phe Ser Leu Thr Ser Gly Thr Ser Val
465                 470                 475                 480
Val Arg Gly Pro Gly Phe Thr Gly Gly Asp Ile Ile Arg Thr Asn Val
                485                 490                 495
Asn Gly Asn Val Leu Ser Met Ser Leu Asn Phe Ser Asn Thr Ser Leu
                500                 505                 510
Gln Arg Tyr Arg Val Arg Val Arg Tyr Ala Ala Ser Gln Thr Met Val
            515                 520                 525
Met Arg Val Asn Val Gly Gly Ser Thr Thr Phe Asp Gln Gly Phe Pro
530                 535                 540
Ser Thr Met Ser Ala Asn Gly Ser Leu Thr Ser Gln Ser Phe Arg Phe
545                 550                 555                 560
Ala Glu Phe Pro Val Gly Ile Ser Thr Ser Gly Ser Gln Thr Ala Gly
                565                 570                 575
Ile Ser Ile Ser Asn Asn Pro Gly Arg Gln Thr Phe His Leu Asp Arg
            580                 585                 590
Ile Glu Phe Ile Pro Val Asp Ala Thr Phe Glu Ala Glu Tyr Asp Leu
            595                 600                 605
Glu Arg Ala Gln Lys Ala Val Asn Ser Leu Phe Thr Ser Ser Asn Gln
    610                 615                 620
Ile Glu Leu Lys Thr Asp Val Thr Asp Tyr His Ile Asp Gln Val Ser
625                 630                 635                 640
Asn Leu Val Asp Cys Leu Ser Asp Glu Phe Cys Leu Asp Glu Lys Arg
                645                 650                 655
Glu Leu Ser Glu Lys Val Lys His Ala Lys Arg Leu Ser Asp Glu Arg
            660                 665                 670
Asn Leu Leu Gln Asp Pro Asn Phe Arg Gly Ile Asn Arg Gln Pro Asp
        675                 680                 685
Arg Gly Trp Arg Gly Ser Thr Asp Ile Thr Ile Gln Gly Gly Asp Asp
690                 695                 700
Val Phe Lys Glu Asn Tyr Val Thr Leu Pro Gly Thr Phe Asp Glu Cys
705                 710                 715                 720
Tyr Pro Thr Tyr Leu Tyr Gln Lys Ile Asp Glu Ser Lys Leu Lys Ala
                725                 730                 735
Tyr Asn Arg Tyr Gln Leu Arg Gly Tyr Ile Glu Asp Ser Gln Asp Leu
            740                 745                 750
Glu Ile Tyr Leu Ile Arg Tyr Asn Ala Lys His Glu Thr Val Asn Val
        755                 760                 765
Pro Gly Thr Gly Ser Leu Trp Pro Leu Ser Val Glu Ser Pro Ile Gly
770                 775                 780
Arg Cys Gly Glu Pro Asn Arg Cys Val Pro His Leu Glu Trp Asn Pro
785                 790                 795                 800
Asp Leu Asp Cys Ser Cys Arg Asp Gly Glu Lys Cys Ala His His Ser
                805                 810                 815
His His Phe Ser Leu Asp Ile Asp Val Gly Cys Thr Asp Leu Gln Glu
            820                 825                 830
Asp Leu Gly Val Trp Val Val Phe Lys Ile Lys Thr Gln Glu Gly Tyr
            835                 840                 845
Ala Arg Leu Gly Asn Leu Glu Phe Ile Glu Glu Lys Pro Leu Ile Gly
    850                 855                 860
Glu Ala Leu Ser Arg Val Lys Arg Ala Glu Lys Lys Trp Arg Asp Lys
865                 870                 875                 880
```

|       |       |       |       |       |       |       |       |       |       |       |       |       |       |       |
|-------|-------|-------|-------|-------|-------|-------|-------|-------|-------|-------|-------|-------|-------|-------|
| Arg   | Glu   | Lys   | Leu   | Gln   | Leu   | Glu   | Thr   | Lys   | Arg   | Val   | Tyr   | Thr   | Glu   | Ala   | Lys |
|       |       |       |       | 885   |       |       |       | 890   |       |       |       |       |       | 895   |
| Glu   | Ala   | Val   | Asp   | Ala   | Leu   | Phe   | Val   | Asp   | Ser   | Gln   | Tyr   | Asp   | Arg   | Leu   | Gln |
|       |       |       | 900   |       |       |       |       | 905   |       |       |       |       | 910   |       |
| Ala   | Asp   | Thr   | Asn   | Ile   | Gly   | Met   | Ile   | His   | Ala   | Ala   | Asp   | Arg   | Leu   | Val   | His |
|       |       | 915   |       |       |       |       | 920   |       |       |       |       | 925   |       |       |
| Gln   | Ile   | His   | Glu   | Ala   | Tyr   | Leu   | Pro   | Glu   | Leu   | Pro   | Phe   | Ile   | Pro   | Gly   | Ile |
|       |       | 930   |       |       |       | 935   |       |       |       |       | 940   |       |       |       |
| Asn   | Val   | Val   | Ile   | Phe   | Glu   | Glu   | Leu   | Glu   | Asn   | Arg   | Ile   | Ser   | Thr   | Ala   | Leu |
| 945   |       |       |       |       | 950   |       |       |       |       | 955   |       |       |       |       | 960 |
| Ser   | Leu   | Tyr   | Asp   | Ala   | Arg   | Asn   | Val   | Ile   | Lys   | Asn   | Gly   | Asp   | Phe   | Asn   | Asn |
|       |       |       |       | 965   |       |       |       |       | 970   |       |       |       |       | 975   |
| Gly   | Leu   | Ser   | Cys   | Trp   | Asn   | Val   | Lys   | Gly   | His   | Val   | Asp   | Val   | Val   | Glu   | Gln |
|       |       |       | 980   |       |       |       |       | 985   |       |       |       |       |       | 990   |
| Asn   | Asn   | His   | Arg   | Ser   | Val   | Leu   | Val   | Val   | Pro   | Glu   | Trp   | Glu   | Ala   | Glu   | Val |
|       |       |       | 995   |       |       |       | 1000  |       |       |       |       |       | 1005  |       |
| Ser   | Gln   | Thr   | Ile   | Arg   | Val   | Cys   | Pro   | Gly   | Arg   | Gly   | Tyr   | Ile   | Leu   | Arg   | Val |
|       |       | 1010  |       |       |       |       | 1015  |       |       |       |       | 1020  |       |       |
| Thr   | Ala   | Tyr   | Lys   | Glu   | Gly   | Tyr   | Gly   | Glu   | Gly   | Cys   | Val   | Thr   | Ile   | His   | Glu |
| 1025  |       |       |       |       | 1030  |       |       |       |       | 1035  |       |       |       |       | 1040 |
| Ile   | Glu   | Asn   | Asn   | Thr   | Asp   | Glu   | Leu   | Lys   | Phe   | Lys   | Asn   | Cys   | Glu   | Glu   | Glu |
|       |       |       |       | 1045  |       |       |       |       | 1050  |       |       |       |       | 1055  |
| Glu   | Val   | Tyr   | Pro   | Thr   | Asp   | Thr   | Gly   | Thr   | Cys   | Asn   | Asp   | Tyr   | Thr   | Ala   | His |
|       |       |       |       | 1060  |       |       |       |       | 1065  |       |       |       |       | 1070  |
| Gln   | Gly   | Thr   | Ala   | Gly   | Ser   | Thr   | Asp   | Ser   | Cys   | Asn   | Ser   | Arg   | Asn   | Ile   | Arg |
|       |       |       | 1075  |       |       |       |       | 1080  |       |       |       |       | 1085  |       |
| Tyr   | Glu   | Asp   | Ala   | Tyr   | Glu   | Met   | Asn   | Thr   | Thr   | Ala   | Ser   | Val   | Asn   | Tyr   | Lys |
|       |       | 1090  |       |       |       |       | 1095  |       |       |       |       | 1100  |       |       |
| Pro   | Thr   | Tyr   | Glu   | Glu   | Glu   | Arg   | Tyr   | Thr   | Asp   | Val   | Gln   | Gly   | Asp   | Asn   | His |
| 1105  |       |       |       |       |       | 1110  |       |       |       |       | 1115  |       |       |       | 1120 |
| Cys   | Glu   | Tyr   | Asp   | Arg   | Gly   | Tyr   | Val   | Asn   | Tyr   | Arg   | Pro   | Val   | Pro   | Ala   | Gly |
|       |       |       |       | 1125  |       |       |       |       | 1130  |       |       |       |       | 1135  |
| Tyr   | Val   | Thr   | Lys   | Glu   | Leu   | Glu   | Tyr   | Phe   | Pro   | Glu   | Thr   | Asp   | Lys   | Val   | Trp |
|       |       |       | 1140  |       |       |       |       | 1145  |       |       |       |       | 1150  |       |
| Ile   | Glu   | Ile   | Gly   | Glu   | Thr   | Glu   | Gly   | Lys   | Phe   | Ile   | Val   | Asp   | Asn   | Val   | Glu |
|       |       |       | 1155  |       |       |       |       | 1160  |       |       |       |       | 1165  |       |
| Leu   | Leu   | Leu   | Met   | Glu   | Glu   |       |       |       |       |       |       |       |       |       |
|       |       |       | 1170  |       |       |       |       |       |       |       |       |       |       |       |

( 2 ) INFORMATION FOR SEQ ID NO:4:

( i ) SEQUENCE CHARACTERISTICS:
        ( A ) LENGTH: 3522 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis
        ( B ) STRAIN: aizawai
        ( C ) INDIVIDUAL ISOLATE: PS81A2

( v i i ) IMMEDIATE SOURCE:
        ( A ) LIBRARY: Lambdagem - 11 (tm) Library of August Sick
        ( B ) CLONE: 81A2

( x i ) SEQUENCE DESCRIPTION: SEQ ID NO:4:

| | | | | | |
|---|---|---|---|---|---|
| ATGGAGAATA | ATATTGAAAA | TCAATGCATA | CCTTACAATT | GTTTAAATAA | TCCTGAAGTA | 60
| GAGATATTAG | GGATTGAAAG | GTCAAATAGT | AACGTAGCAG | CAGAAATCGG | CTTGGGGCTT | 120
| AGTCGTCTGC | TCGTTTCCCG | AATTCCACTA | GGGGATTTTA | TACTTGGCTT | GTTTGATGTA | 180
| ATATGGGGGG | CTATAGGTCC | TTCACAATGG | GATATATTTT | TAGAGCAAAT | TGAGCTATTG | 240
| ATCGGCCAAA | GAATAGAGGA | ATTCGCTAGG | AATCAGGCAA | TTTCTAGATT | ACAAGGGCTA | 300
| AGCAATCTTT | ACCGAATTTA | CACAAATGCT | TTTAAAAACT | GGGAAGTAGA | TCCTACTAAT | 360
| CCAGCATTAA | GAGAAGAGAT | GCGTATTCAA | TTTAATGACA | TGAACAGTGC | TCTTACAACA | 420
| GCTATTCCTC | TTTTTTCAGT | TCAAGGTTAT | GAAATTCCTC | TTTTATCAGT | ATATGTTCAA | 480
| GCTGCAAATT | TACATTTATC | GGTTTTGAGA | GATGTTTCAG | TGTTTGGACA | ACGTTGGGGA | 540
| TTTGATGTAG | CAACAATCAA | TAGTCGTTAT | AATGATTTAA | CTAGGCTTAT | TGGCGAATAT | 600
| ACTGATTATG | CTGTACGTTG | GTATAATACG | GGGTTAAATC | GTTACCACG | TAATGAAGGG | 660
| GTACGAGGAT | GGGCAAGATT | TAATAGGTTT | AGAAGAGAGT | TAACAATATC | AGTATTAGAT | 720
| ATTATTTCTT | TTTTCCAAAA | TTACGATTCT | AGATTATATC | CAATTCCGAC | AATCTATCAA | 780
| TTAACGCGGG | AAGTATATAC | AGATCCGGTA | ATTAATATAA | CTGATTATAG | AGTTACCCCA | 840
| AGTTTCGAGA | GTATTGAAAA | TTCAGCTATT | AGAAGTCCCC | ATCTTATGGA | TTTCTTAAAT | 900
| AATATAATTA | TTGACACTGA | TTTAATTAGA | GGCGTTCACT | ATTGGGCGGG | GCATCGTGTA | 960
| ACTTCTCATT | TTACCGGTAG | TTCGCAAGTG | ATAAGCTCCC | CTCAATACGG | GATAACTGCA | 1020
| AACGCAGAAC | CGAGTCGAAC | TATTGCTCCT | AGCACTTTTC | CAGGTCTTAA | TCTATTTTAT | 1080
| AGAACACTAT | CAGACCCTTT | CTTCCGAAGA | TCCGATAATA | TTATGCCAAC | ATTAGGAATA | 1140
| AATGTAGTGC | AGGGGGTAGG | ATTCATTCAA | CCAAATAATG | GTGAAGTTCT | ATATAGAAGG | 1200
| AGAGGAACAG | TAGATTCTCT | TGATGAGTTG | CCAATTGACG | GTGAGAATTC | ATTAGTTGGA | 1260
| TATAGTCATA | GATTAAGTCA | CGTTACATTA | ACCAGGTCGT | TATATAATAC | TAATATAACT | 1320
| AGCTTGCCAA | CATTTGTTTG | GACACATCAC | AGTGCTACTG | ATCGAAATAT | AATCTATCCG | 1380
| GATGTAATTA | CACAAATACC | ATTGGTAAAA | TCATTCTCCC | TTACTTCAGG | TACCTCTGTA | 1440
| GTCAGAGGCC | CAGGATTTAC | AGGAGGGGAT | ATCATCCGAA | CTAACGTTAA | TGGTAATGTA | 1500
| CTAAGTATGA | GTCTTAATTT | TAGTAATACA | TCATTACAGC | GGTATCGCGT | GAGAGTTCGT | 1560
| TATGCTGCTT | CTCAAACAAT | GGTCATGAGA | GTAAATGTTG | GAGGGAGTAC | TACTTTTGAT | 1620
| CAAGGATTCC | CTAGTACTAT | GAGTGCAAAT | GGGTCTTTGA | CATCTCAATC | ATTTAGATTT | 1680
| GCAGAATTTC | CTGTAGGCAT | TAGTACATCT | GGCAGTCAAA | CTGCTGGAAT | AAGTATAAGT | 1740
| AATAATCCAG | GTAGACAAAC | GTTTCACTTA | GATAGAATTG | AATTTATCCC | AGTTGATGCA | 1800
| ACATTTGAAG | CAGAATATGA | TTTAGAAAGA | GCACAAAAGG | CGGTGAATTC | GCTGTTTACT | 1860
| TCTTCCAATC | AAATCGAGTT | AAAAACAGAT | GTGACGGATT | ATCATATTGA | TCAAGTATCC | 1920
| AATTTAGTAG | ATTGTTTATC | CGATGAATTT | TGTCTGGATG | AAAAGCGAGA | ATTGTCCGAG | 1980
| AAAGTCAAAC | ATGCGAAGCG | ACTCAGTGAT | GAGCGGAATT | TACTTCAAGA | TCCAAACTTC | 2040
| AGAGGGATCA | ATAGGCAACC | AGACCGTGGC | TGGAGAGGAA | GTACGGATAT | TACCATCCAA | 2100
| GGAGGAGATG | ACGTATTCAA | AGAGAATTAC | GTCACACTAC | CAGGTACCTT | TGATGAGTGC | 2160
| TATCCAACGT | ATTTGTATCA | AAAAATAGAT | GAGTCGAAAT | TAAAAGCCTA | TAACCGTTAC | 2220
| CAATTAAGAG | GGTATATCGA | AGATAGTCAA | GACTTAGAAA | TCTATTTAAT | TCGCTACAAT | 2280
| GCAAAACACG | AAACAGTAAA | TGTACCAGGT | ACGGGTTCCT | TATGGCCGCT | TTCAGTCGAA | 2340
| AGTCCAATTG | GAAGGTGTGG | AGAACCGAAT | CGGTGTGTGC | CACACCTTGA | ATGGAATCCT | 2400
| GATTTAGATT | GTTCCTGCAG | AGACGGGGAA | AAATGTGCAC | ATCATTCCCA | TCATTTCTCC | 2460

```
TTGGACATTG ATGTTGGATG CACAGACTTG CAAGAGGATC TAGGCGTGTG GGTTGTATTC    2520

AAGATTAAGA CGCAGGAAGG TTATGCAAGA TTAGGAAATC TGGAATTTAT CGAAGAGAAA    2580

CCATTAATTG GAGAAGCACT GTCTCGTGTG AAGAGAGCGG AAAAAAATG GAGAGACAAA     2640

CGGGAAAAAC TACAATTGGA AACAAAACGA GTATATACAG AGGCAAAGA AGCTGTGGAT     2700

GCTTTATTCG TAGATTCTCA ATATGATAGA TTACAAGCAG ATACAAACAT TGGTATGATT    2760

CATGCGGCAG ATAGACTTGT TCATCAGATC CACGAGGCTT ATCTTCCAGA ACTACCTTTC    2820

ATTCCAGGAA TAAATGTGGT GATTTTTGAA GAATTAGAAA ACCGTATTTC TACTGCATTA    2880

TCCCTATATG ATGCGAGAAA TGTCATTAAA AATGGCGATT TCAATAATGG CTTATCATGC    2940

TGGAACGTGA AAGGGCATGT AGATGTAGTA GAACAAAACA ACCACCGTTC GGTCCTTGTT    3000

GTCCGGAAT GGGAAGCAGA AGTGTCACAA ACAATTCGTG TCTGTCCGGG GCGTGGCTAT     3060

ATCCTCCGTG TTACAGCGTA CAAAGAGGGA TATGGAGAAG GTTGCGTAAC CATCCATGAG    3120

ATCGAGAACA ATACAGACGA ACTAAAATTT AAAAACTGTG AAGAAGAGGA AGTGTATCCA    3180

ACGGATACAG GAACGTGTAA TGATTATACT GCACACCAAG GTACAGCAGG ATCCACAGAT    3240

TCATGTAATT CCCGTAATAT CAGATATGAG GATGCATATG AAATGAATAC TACAGCATCT    3300

GTTAATTACA AACCGACTTA CGAAGAAGAA AGGTATACAG ATGTACAAGG AGATAATCAT    3360

TGTGAATATG ACAGAGGGTA TGTGAATTAT CGACCAGTAC CAGCTGGTTA TGTGACAAAA    3420

GAATTAGAGT ACTTCCCAGA AACCGATAAG GTATGGATTG AGATCGGAGA AACGGAAGGG    3480

AAGTTTATTG TAGACAATGT CGAATTACTC CTTATGGAGG AA                       3522
```

BACILLUS THURINGIENSIS ISOLATES ACTIVE AGAINST LEPIDOPTERAN PESTS, AND GENES ENCODING NOVEL LEPIDOPTERAN-ACTIVE TOXINS

CROSS-REFERENCE TO A RELATED APPLICATION

This is a division of application Ser. No. 07/904,243, filed Jun. 25, 1992, now issued as U.S. Pat. No. 5,206,166, which is a division of application Ser. No. 07/451,389, filed Dec. 14, 1989, now issued as U.S. Pat. No. 5,164,180, which was a continuation-in-part of Ser. No. 07/353,860, filed May 18, 1989, now abandoned.

BACKGROUND OF THE INVENTION

The most widely used microbial pesticides are derived from the bacterium *Bacillus thuringiensis*. This bacterial agent is used to control a wide range of leaf-eating caterpillars and beetles, as well as mosquitos. *Bacillus thuringiensis* produces a proteinaceous parasporal body or crystal which is toxic upon ingestion by a susceptible insect host. For example, *B. thuringiensis* subsp. *kurstaki* HD-1 produces a crystal inclusion consisting of a biotoxin called a delta toxin which is toxic to the larvae of a number of lepidopteran insects. The cloning, sequencing, and expression of this *B.t.* crystal protein gene in *Escherichia coli* has been described in the published literature (Schnepf, H. E. and Whitely, H. R. [1981] Proc. Natl. Acad. Sci. USA 78:2893–2897; Schnepf et al.). U.S. Pat. No. 4,448,885 and U.S. Pat. No. 4,467,036 both disclose the expression of *B.t.* crystal protein in *E. coli*.

BRIEF SUMMARY OF THE INVENTION

The subject invention concerns novel *Bacillus thuringiensis* isolates designated *B.t.* PS81A2 and PS81RR1 which have activity against all lepidopteran pests tested.

Also disclosed and claimed are novel toxin genes which express toxins toxic to lepidopteran insects. These toxin genes can be transferred to suitable hosts via a plasmid vector.

Specifically, the invention comprises novel *B.t.* isolates denoted *B.t.* PS81A2 and PS81RR1, mutants thereof, and novel delta endotoxin genes derived from these *B.t.* isolates which encode proteins which are active against lepidopteran pests. More specifically, the gene in *B.t.* PS81A2 encodes a 133,601 dalton endoxin, whereas the gene in *B.t.* PS81RR1 encodes a 133,367 dalton endotoxin.

BRIEF DESCRIPTION OF THE SEQUENCES

SEQ ID NO. 1 discloses the amino acid sequence of the novel toxin expressed by PS81RR1.

SEQ ID NO. 2 discloses the DNA encoding the novel toxin expressed by PS81RR1.

SEQ ID NO. 3 discloses the amino acid sequence of the novel toxin expressed by PS81A2.

SEQ ID NO. 4 discloses the DNA encoding the novel toxin expressed by PS81A2.

BRIEF DESCRIPTION OF THE DRAWINGS

FIG. 1 shows agarose gel electrophoresis of plasmid preparations from *B.t.* PS81A2, *B.t.* PS81RR1, and *B.t.* HD-1.

DETAILED DESCRIPTION OF THE INVENTION

The novel toxin genes of the subject invention were obtained from novel lepidopteran-active *B. thuringiensis* (*B.t.*) isolates designated PS81A2 and PS81RR1.

Characteristics of *B.t.* PS81A2 and PS81RR1

Colony morphology—Large colony, dull surface, typical *B.t.*
Vegetative cell morphology—typical *B.t.*
Flagellar serotype—7, aizawai.
Intracellular inclusions—sporulating cells produce a bipyramidal crystal.
Plasmid preparations—agarose gel electrophoresis of plasmid preparations distinguishes *B.t.* PS81A2 and PS81RR1 from *B.t.* HD-1 and other *B.t.* isolates. See FIG. 1.
Alkali-soluble proteins—*B.t.* PS81A2 and PS81RR1 produce 133,601 and 133,367 dalton proteins, respectively.
Unique toxins—the 133,601 and 133,367 dalton toxins are different from any previously identified.
Activity—*B.t.* PS81A2 and PS81RR1 both kill all Lepidoptera tested (*Trichoplusia ni*, *Spodoptera exigua*, and *Plutella xylostella*).
Bioassay procedures:
  *Spodoptera exigua*—dilutions are prepared of a spore and crystal pellet, mixed with USDA Insect Diet (Technical Bulletin 1528, U.S. Department of Agriculture) and poured into small plastic trays. Neonate *Spodoptera exigua* larvae are placed on the diet mixture and held at 25° C. Mortality is recorded after six days.
  Other insects—dilutions and diet are prepared in the same manner as for the *Spodoptera exigua* bioassay. Fourth instar larvae are used, and mortality is recorded after eight days.

*B. thuringiensis* PS81A2, NRRL B-18457, and *B. thuringiensis* PS81RR1, NRRL B-18458, and mutants thereof, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. *B.t.* PS81A2 and *B.t.* PS81RR1, and mutants thereof, can be used to control lepidopteran pests.

A subculture of *B.t.* PS81A2 and PS81RR1 and the *E. coli* hosts harboring the toxin genes of the invention, were deposited in the permanent collection of the Northern Research Laboratory, U.S. Department of Agriculture, Peoria, Ill., USA. The accession numbers and deposit dates are as follows:

| Subculture | Accession Number | Deposit Date |
|---|---|---|
| *B.t.* PS81A2 | NRRL B-18457 | March 14, 1989 |
| *B.t.* PS81RR1 | NRRL B-18458 | March 14, 1989 |

| Subculture | Accession Number | Deposit Date |
|---|---|---|
| E. coli (NM522)(pMYC389) | NRRL B-18448 | February 24, 1989 |
| E. coli (NM522)(pMYC390) | NRRL B-18449 | February 24, 1989 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin genes of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a B.t. gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The $B.t.$ gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae, Actinomycetales, and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the $B.t.$ gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans* and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W.H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81A2 and PS81RR1 can be made by procedures well known in the art. For example, an asporogenous mutant can be obtained through ethylmethane sulfonate (EMS) mutagenesis of PS81A2 and PS81RR1. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1—CULTURING *B.t.* PS81A2 AND PS81RR1

A subculture of *B.t.* PS81A2 and PS81RR1, or mutants thereof, can be used to inoculate the following medium, a peptone, glucose, salts medium.

| | |
|---|---|
| Bacto Peptone | 7.5 g/l |
| Glucose | 1.0 g/l |

| -continued | |
| --- | --- |
| KH₂PO₄ | 3.4 g/l |
| K₂HPO₄ | 4.35 g/l |
| Salt Solution | 5.0 ml/l |
| CaCl₂ Solution | 5.0 ml/l |
| Salts Solution (100 ml) | |
| MgSO₄.7H₂O | 2.46 g |
| MnSO₄.H₂O | 0.04 g |
| ZnSO₄.7H₂O | 0.28 g |
| FeSO₄.7H₂O | 0.40 g |
| CaCl₂ Solution (100 ml) | |
| CaCl₂.2H₂O | 3.66 g |
| pH 7.2 | |

The salts solution and CaCl₂ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The $B.t.$ spores and/or crystals, obtained in the above fermentation, can be isolated by procedures well known in the art. A frequently-used procedure is to subject the harvested fermentation broth to separation techniques, e.g., centrifugation.

EXAMPLE 2—CLONING OF NOVEL TOXIN GENE FROM ISOLATE PS81A2 AND TRANSFORMATION INTO Escherichia coli Total cellular DNA was prepared from $B.t.$ cells grown to a low optical density ($OD_{600}=1.0$). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium gradient.

Total cellular DNA from PS81A2 and $B.t.k.$ HD-1 was digested with EcoRI and separated by electrophoresis on a 0.8% Agarose-TAE-buffered gel. A Southern blot of the gel was probed with the NsiI to NsiI fragment of the toxin gene contained in plasmid pM3,130-7 of NRRL B-18332 and the NsiI to KpnI fragment of the "4.5 Kb class" toxin gene (Kronstad and Whitely [1986] Gene USA 43:29–40). These two fragments were combined and used as the probe. Results show that hybridizing fragments of PS81A2 are distinct from those of HD-1. Specifically, a 3.0 Kb hybridizing band in PS81A2 was detected instead of the 3.8 Kb and 1.8 Kb hybridizing bands seen in HD-1.

Two hundred micrograms of PS81A2 total cellular DNA was digested with EcoRI and separated by electrophoresis on a preparative 0.8% Agarose-TAE gel. The 2.5 Kb to 3.5 Kb region of the gel was cut out and the DNA from it was electroeluted and concentrated using an ELUTIP TM-d (Schleicher and Schuell, Keene, N.H.) ion exchange column. The isolated EcoRI fragments were ligated to LAMBDA ZAP TM EcoRI arms (Stratagene Cloning Systems, La Jolla, Calif.) and packaged using Gigapak GOLD TM (Stratagene) extracts. The packaged recombinant phage were plated with $E.$ $coli$ strain BB4 (Stratagene) to give high plaque density. The plaques were screened by standard nucleic acid hybridization procedure with radiolabeled probe. The plaques that hybridized were purified and re-screened at a lower plaque density. The resulting purified phage were grown with R408 M13 helper phage (Stratagene) and the recombinant BlueScript TM (Stratagene) plasmid was automatically excised and packaged. The "phagemid" was re-infected in XL1-Blue $E.$ $coli$ cells (Stratagene) as part of the automatic excision process. The infected XL1-Blue cells were screened for ampicillin resistance and the resulting colonies were analyzed by standard miniprep procedure to find the desired plasmid. The plasmid, designated pM6,31-1, contains an approximate 3.0 Kb EcoRI insert and was sequenced using Stratagene's T7 and T3 primers plus a set of existing $B.t.$ endotoxin gene oligonucleotide primers. About 1.8 Kb of the toxin gene was sequenced, and data analysis comparing PS81A2 to other cloned $B.t.$ endotoxin genes showed that the PS81A2 sequence was unique. A synthetic oligonucleotide was constructed to one of the regions in the PS81A2 sequence that was least homologous relative to other exiting $B.t.$ endotoxin genes.

PS81A2 total cellular DNA partially digested with Sau3A and fractionated by electrophoresis into a mixture of 9–23 Kb fragments on a 0.6% agarose-TAE gel was ligated into Lambda DASH TM (Stratagene). The packaged phage at a high titer were plated on P2392 $E.$ $coli$ cells (Stratagene) and screened using the radiolabeled synthetic oligonucleotide (aforementioned) as a nucleic acid hybridization probe. Hybridizing plaques were rescreened at a lower plaque density. A single purified hybridizing plaque was used to infect P2392 $E.$ $coli$ cells in liquid culture for preparation of phage for DNA isolation. DNA was isolated by standard procedures. Preparative amounts of recombinant phage DNA were digested with SalI (to release the inserted DNA from lambda arms) and separated by electrophoresis on a 0.6% Agarose-TAE gel. The large fragments, electroeluted and concentrated as described above, were ligated to SalI-digested and dephosphorylated pUC19 (NEB). The ligation mixture was introduced by transformation into $E.$ $coli$ DH5(alpha) competent cells (BRL) and plated on LB agar containing ampicillin, isopropyl-(Beta)-D-thiogalactoside (IPTG) and 5-Bromo-4-Chloro-3-indolyl-(Beta)-D-galactoside (XGAL). White colonies (with insertions in the (Beta)-galactosidase gene of pUC19) were subjected to standard miniprep procedures to isolate the plasmid, designated pM4,122-3. The full length toxin gene was sequenced by using oligonucleotide primers made to the "4.5 Kb class" toxin gene and by "walking" with primers made to the sequence of PS81A2.

The plasmid pM4,122-3 contains about 15 Kb of PS81A2 DNA including the 3.522 Kb which encodes the 133,601 dalton endotoxin. The ORF of the PS81A2 toxin gene was isolated from pM4,122-3 and subcloned into the Bacillus shuttle vector pBC1ac as a 5.5 Kb blunt-ended DraIII fragment. $E.$ $coli$ NM522 cells were transformed and plated on LB agar supplemented with ampicillin. The resulting colonies were analyzed by standard miniprep procedures to isolate plasmids that contained the insert. The desired plasmid, pMYC389, contains the coding sequence of the PS81A2 toxin gene.

EXAMPLE 3—CLONING OF NOVEL TOXIN GENE FROM ISOLATE PS81RR1 AND TRANSFORMATION INTO *Escherichia coli*

Total cellular DNA was prepared from *B.t.* cells grown to a low optical density ($OD_{600}=1.0$). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium chloride gradient.

Total cellular DNA from PS81RR1 and *B.t.k.* HD-1 was digested with EcoRI and separated by electrophoresis on a 0.8% Agarose-TAE-buffered gel. A Southern blot of the gel was probed with the NsiI to NsiI fragment of the toxin gene contained in plasmid pM3,130-7 of NRRL B-18332 and the NsiI to KpnI fragment of the "4.5 Kb class" toxin gene (Kronstad and Whitely [1986] Gene USA 43:29–40). These two fragments were combined and used as the probe. Results show that hybridizing fragments of PS81RR1 are distinct from those of HD-1. Specifically, a 2.3 Kb hybridizing band in PS81RR1 was detected instead of the 3.8 Kb and 1.8 Kb hybridizing bands seen in HD-1.

Two hundred micrograms of PS81RR1 total cellular DNA was digested with EcoRI and separated by electrophoresis on a preparative 0.8% Agarose-TAE gel. The 2.2 Kb to 2.4 Kb region of the gel was cut out and the DNA from it was electroeluted and concentrated using an ELUTIP TM-d (Schleicher and Schuell, Keene, N.H.) ion exchange column. The isolated EcoRI fragments were ligated to LAMBDA ZAP TM EcoRI arms (Stratagene Cloning Systems, La Jolla, Calif.) and packaged using Gigapak GOLD TM (Stratagene) extracts. The packaged recombinant phage were plated with *E. coli* strain BB4 (Stratagene) to give high plaque density. The plaques were screened by standard nucleic acid hybridization procedure with radiolabeled probe. The plaques that hybridized were purified and re-screened at a lower plaque density. The resulting purified phage were grown with R408 M13 helper phage (Stratagene) and the recombinant BlueScript TM (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by standard miniprep procedure to find the desired plasmid. The plasmid, designated pM3,31-3, contains an approximate 2.3 Kb EcoRI insert and was sequenced using Stratagene's T7 and T3 primers plus a set of existing *B.t.* endotoxin oligonucleotide primers. About 600 bp of the toxin gene was sequenced, and data analysis comparing PS81RR1 to other cloned *B.t.* endotoxin genes showed that the PS81RR1 sequence was unique. A synthetic oligonucleotide was constructed to one of the regions in the PS81RR1 sequence that was least homologous relative to other existing *B.t.* endotoxin genes.

PS81RR1 total cellular DNA partially digested with Sau3A and fractionated by electrophoresis into a mixture of 9–23 Kb fragments on a 0.6% agarose-TAE gel was ligated into Lambda GEM TM-11 (PROMEGA). The packaged phage at a high titer were plated on P2392 *E. coli* cells (Stratagene) and screened using the radiolabeled synthetic oligonucleotide (aforementioned) as a nucleic acid hybridization probe. Hybridizing plaques were rescreened at a lower plaque density. A single purified hybridizing plaque was used to infect P2392 *E. coli* cells in liquid culture for preparation of phage for DNA isolation. DNA was isolated by standard procedures. Preparative amounts of recombinant phage DNA were digested with SalI, to release the inserted DNA from lambda arms, and separated by electrophoresis on a 0.6% Agarose-TAE gel. The large fragments, electroeluted and concentrated as described above, were ligated to SalI-digested and dephosphorylated pUC19 (NEB). The ligation mixture was introduced by transformation into *E. coli* DH5(alpha) competent cells (BRL) and plated on LB agar containing ampicillin, isopropyl-(Beta)-D-thiogalactoside (IPTG) and 5-Bromo-4-Chloro-3-indolyl-(Beta)-D-galactoside (XGAL). White colonies (with insertions in the (Beta)-galactosidase gene of pUC19) were subjected to standard miniprep procedures to isolate the plasmid, designated pM1,RR1-A. The full length toxin gene was sequenced by using oligonucleotide primers made to the "4.5 Kb class" toxin gene and by "walking" with primers made to the sequence of PS81RR1.

The plasmid pM1,RR1-A contains about 13 Kb of PS81RR1 DNA including the 3.540 Kb which encodes the 133,367 dalton endotoxin. The ORF of the PS81RR1 toxin gene was isolated from pM1,RR1-A on a 3.8 Kb NdeI fragment and ligated into the Bacillus shuttle vector pBC1ac. *E. coli* NM522 cells were transformed and the resulting colonies were analyzed by standard miniprep procedures to isolate plasmids that contained the correct insert. The desired plasmid, pMYC390, contains the coding sequence of the PS81RR1 toxin gene.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., New England Biolabs, Beverly, Mass., or Boehringer-Mannheim, Indianapolis, Ind. The enzymes are used according to the instructions provided by the supplier.

Plasmid pMYC386 containing the *B.t.* toxin genes, can be removed from the transformed host microbes by use of standard well-known procedures. For example, *E. coli* NRRL B-18449 can be subjected to cleared lysate isopycnic density gradient procedures, and the like, to recover pMYC386.

EXAMPLE 4—INSERTION OF TOXIN GENES INTO PLANTS

The novel genes coding for the novel insecticidal toxins, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 5—CLONING OF NOVEL *B. thuringiensis* GENES INTO BACULOVIRUSES

The novel genes of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequences encoding the novel *B.t.* toxin genes are shown in SEQ ID NO. 2 and SEQ ID NO. 4. The deduced amino acid sequences are shown in SEQ ID NO. 1 and SEQ ID NO. 3.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W=C if Z is C or T
Z=A, G, C or T if W is C
Z=A or G if W is A
QR=TC if S is A, G, C or T; alternatively QR=AG if S is T or C
J=A or G
K=T or C
L=A, T, C or G
M=A, C or T The above shows that the novel amino acid sequences of the *B.t.* toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is retained to some degree.

---

We claim:

1. *Bacillus thuringiensis* PS81RR1, having the identifying characteristics of NRRL B-18458, or a mutant thereof, having activity against insect pests of the order Lepidoptera.

2. A purified toxin active against lepidopteran insects having the amino acid sequence shown in SEQ ID NO. 1 or SEQ ID NO. 3, or a variant thereof which retains the biological activity of said toxin.

3. An insecticidal composition comprising treated, substantially intact cells containing an intracellular toxin, which toxin is a result of expression of a *Bacillus thuringiensis* toxin gene which encodes a polypeptide toxin active against lepidopteran pests, wherein said toxin has the amino acid sequence shown in SEQ ID NO. 1 or SEQ ID NO. 3, and wherein said cells have been treated under conditions which prolong the toxic activity when said cells are applied to the environment of said lepidopteran pest.

4. The insecticidal composition, according to claim 3, wherein said treated cells are treated by chemical or physical means to prolong their insecticidal activity in the environment.

5. The insecticidal composition, according to claim 4, wherein said cells are prokaryotes or lower eukaryotes.

6. The insecticidal composition, according to claim 5, wherein said prokaryotic cells are selected from the group consisting of Enterobacteriaceae, Bacillaceae, Rhizobiaceae, Spirillaceae, Lactobacillaceae, Pseudomonadaceae, Azotobacteraceae, Nitrobacteraceae, and Actinomycetales.

7. The insecticidal composition, according to claim 5, wherein said lower eukaryotic cells are selected from the group consisting of Phycomycetes, Ascomycetes, and Basidiomycetes.

8. The insecticidal composition, according to claim 3, wherein said cells are pigmented bacteria, yeast, or fungi.

9. A treated, substantially intact unicellular microorganism containing an intracellular toxin, which toxin is a result of expression in said microorganism of a *Bacillus thuringiensis* toxin gene, said toxin having insecticidal activity against lepidopteran insects, and having the amino acid sequence shown in SEQ ID NO. 1 or SEQ ID NO. 3, wherein said microorganism is treated under conditions which prolong the insecticidal activity when said microorganisms is applied to the environment of said lepidopteran pest.

10. The microorganism, according to claim 9, wherein the microorganism is treated by chemical or physical means to prolong the insecticidal activity in the environment.

11. The microorganism according to claim 9, wherein said microorganism is Pseudomonas and said toxin is a *Bacillus thuringiensis* toxin having the amino acid sequence shown in SEQ ID NO. 1 or SEQ ID NO. 3.

12. A Pseudomonas microorganism, according to claim 11, wherein said microorganism is treated with iodine.

13. The microorganism, according to claim 9, which is *Pseudomonas fluorescens*.

* * * * *